(12) United States Patent
Haeri et al.

(10) Patent No.: US 8,540,369 B2
(45) Date of Patent: Sep. 24, 2013

(54) LED VARIABLE LIGHT SOURCE

(75) Inventors: Mohammad Haeri, Syracuse, NY (US); Eduardo Solessio, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 210 days.

(21) Appl. No.: 12/673,611

(22) PCT Filed: Aug. 15, 2008

(86) PCT No.: PCT/US2008/073232
§ 371 (c)(1),
(2), (4) Date: Feb. 7, 2011

(87) PCT Pub. No.: WO2009/023805
PCT Pub. Date: Feb. 19, 2009

(65) Prior Publication Data
US 2011/0116046 A1    May 19, 2011

Related U.S. Application Data

(60) Provisional application No. 60/965,231, filed on Aug. 16, 2007.

(51) Int. Cl.
*A61B 3/10* (2006.01)
*H01J 7/24* (2006.01)
*G05F 1/00* (2006.01)

(52) U.S. Cl.
USPC ............ 351/221; 315/112; 315/291; 315/294

(58) Field of Classification Search
USPC .......................... 351/221; 315/291, 112, 294
See application file for complete search history.

(56) References Cited

U.S. PATENT DOCUMENTS

| | | | | |
|---|---|---|---|---|
| 6,154,282 A | * | 11/2000 | Lilge et al. | 356/417 |
| 7,133,138 B2 | * | 11/2006 | Horii et al. | 356/497 |
| 2003/0184753 A1 | * | 10/2003 | Ogawa | 356/432 |
| 2005/0254008 A1 | * | 11/2005 | Ferguson et al. | 351/205 |

\* cited by examiner

*Primary Examiner* — Jack Dinh
(74) *Attorney, Agent, or Firm* — Scully, Scott, Murphy & Presser, P.C.

(57) ABSTRACT

An LED variable light source of this invention includes a super luminescent LED for generating a continuous light signal having a logarithmically controllable light intensity maintainable over a broad spectral range. The LED variable light source also includes a light lens for receiving and focusing the generated continuous light signal and a controller for controlling the light signal's intensity and frequency range via a driver interface, constructed and arranged to allow a user to input LED variable light source control inputs.

23 Claims, 5 Drawing Sheets

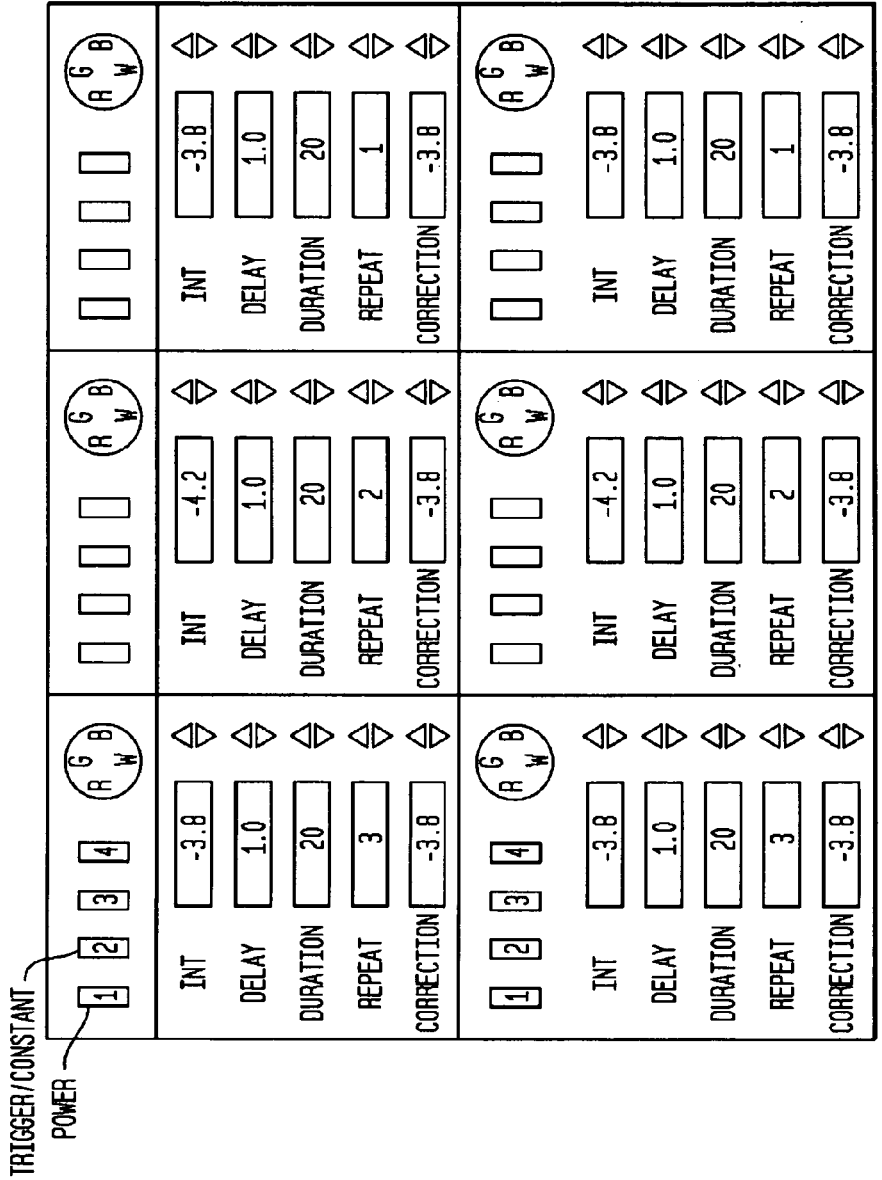

12 CHANNEL CONTROLLER

LED VARIABLE LIGHT SOURCE

CROSS-REFERENCE TO RELATED APPLICATIONS

This application claims the benefit of U.S. Provisional Application No. 60/965,231 filed on Aug. 16, 2007.

GOVERNMENT INTERESTS

The invention was made with Government support under 1004999/33925 awarded by the National Eye Institute. The Government has certain rights in the invention.

BACKGROUND OF THE INVENTION

The present invention relates to light stimulators, and more particularly relates to a novel LED variable light source constructed for use in light stimulators for retinal examinations, and the study (characterization) of light-sensitive cells and devices.

Incandescent light sources, and light emitting diodes (LEDs) are known to be used for applying pulsed light for the stimulation of light sensitive cells during retinal examinations. Currently available instrumentation for implementing retinal examinations uses a combination of lenses, filters, and shutters to direct light from a light source to achieve the retinal stimulation/examination. For example, U.S. Pat. No. 4,618,230, to Ens, et al. ("the '230 patent"), discloses a light stimulator that provides light for stimulating the retina's of a patient's eyes during a visual (retinal) examinations. Light stimulation is required to elicit data concerning retinal functioning during intracellular recordings, electroretinograms (ERGs), electro-oculograms, and other light evoked examinations.

The light stimulator disclosed by the '230 patent utilizes a pulsed light source and light directing means for directing the light generated by the pulsed light source into the patient's eyes (typically to irradiate (stimulate) the retina). The light stimulator also includes attenuator means for selectively attenuating the pulsed light source, photodetector means for capturing an output signal representative of the radiant energy directed into the patient's eyes and signal processing means for receiving and processing the output signal to derive further signals representative of the radiometric or photometric characteristics of the radiant energy. A light shutter comprising first and second shutter leaves affixed to shafts of a first and a second galvanometer is also included with the disclosed light stimulator. Attenuation control means provide for selectively varying current signals applied to the galvanometers to selectively pivot the control leaves thereby selectively varying the light used in an eye examination.

Known instrumentation that includes such known visual stimulators for carrying out electroretinograms, electro-oculograms, and other visually evoked examinations are further known to be bulky and expensive. Moreover, the '230 patent describes that its visual stimulator and incandescent light source further require R, G and B optical filters to filter the pulsed light generated in the incandescent light source to realize the proper wavelength of the light to be used for an examination, where wavelength defines color.

These restrictions yield losses in terms of the power generated by the incandescent or arc lamps and the power delivered to each target. The radiant power of incandescent or arc lamps extends from the ultraviolet (UV) to the infrared end of the spectrum, covering the visual spectrum in its entirety. Monochromatic flashes used for visual stimulation in clinical and basic research studies only require a narrow bandwidth, 10 to 20 nm wide. Thus the color filters block over 90% of the power emitted by the incandescent or arc lamps. Put in other words, 90% of the power is wasted by this means. Additional power loss results from the inefficacy of the timing mechanism.

The incandescent light is 'on' for the duration of the experiment or clinical examination. During a flash a mechanical shutter opens and light is delivered to the eye. However the duration of the flashes (which is a few msec in duration) is insignificant when compared to the time the incandescent or arc lamps are on. Thus, a large amount of power is wasted by this means. Incandescent and arc lamps are not designed to operate in pulsed regimes. Another option is using the new generation of 'pulsed' arc lamps, however their cost is several-fold higher than the LED solution we propose and also require color filter option for their operation.

In some known applications requiring light stimulators, or light stimulation, pulsed light-emitting diodes (LEDs) are used in place of more conventional incandescent light sources. Such pulsed LEDs are semiconductor devices that operate within known light stimulators to emit incoherent narrow-spectrum light when electrically biased in the forward direction of the p-n junction, i.e., electroluminescence. Pulsed LEDs are available in colors that represent the entire visual spectrum, with bandwidths of about 20-30 nm. The use of pulsed LEDs in lieu of conventional incandescent lights is particularly attractive to scientists using light stimulators to study visual processes, such as those elicited during electroretinograms, electro-oculograms, and other visually evoked examinations.

Pulsed-LED devices, however, have limitations. Intensity of the flash is governed by the frequency of the pulses. Higher frequency of the pulses results in brighter flashes. Lowering the frequency of the pulses produces dim flashes. At extremely low frequencies the number of pulses is sparse and light-sensitive cells with fast responses may discriminate between pulses. A second limitation at dim levels regards the step-wise rather than continuous regulation of light intensity. One pulse is the lowest intensity possible. The next lowest light intensity would result from two-pulse application and so forth. Selection of a continuous range of intensities is particularly desirable at the low range of intensities.

LEDs are inexpensive as compared with traditional incandescent light sources, and display high power efficiency. LEDs display extremely fast on and off set times, for example, on an order of less than one millisecond. Recent advances in LED technology have realized superluminescent diodes (SLDs), which are edge-emitting semiconductors that operate based on superluminescence principles. SLDs result in a 10-fold increase in luminance (intensity of emission) over conventional LEDs. Moreover, the miniaturization of SLDs affords three or more different SLDs, e.g., R, G, B, on a single chip, or chip package. In one embodiment, an SLD is used that is manufactured by Lamina Ceramics, Westhampton, N.J.

What would be desirable in the art of controlled light sources and light stimulation applications in research and medicine is a LED variable light source comprising an SLD and light source components for controlling the SLD for particular applications requiring retinal stimulation that is more compact, more flexible and more user friendly than conventional light sources embodying a fully electronic construction that overcomes the shortcomings of the prior art.

SUMMARY OF THE INVENTION

To that end, the SLD-based light source of the invention results in a LED variable light source for use as a visual stimulator, such as those used to conduct retinal examinations, e.g., electroretinograms, electro-oculograms, and other visually evoked examinations, constructed in fully electronic and compact form to operate more simply and with more flexibility known light stimulators. The novel LED variable light source of the invention is expected to be ideal for use by individuals and institutions that conduct research and/or retinal examinations with small animals, light sensitive cells (for example, a retina of a human eye) and systems and devices for implementing same. The novel LED variable light source or light stimulator of the invention is controlled by at least two modes. In the first mode the light is controlled by changing the duty cycle of a pulsed signal (>1 MHz) driving the LED; in the second mode it is controlled by a DC source or current or voltage, and is continually driven by the same DC source. Moreover, by virtue of the compact size, electronic control of flash parameters (flash duration, color and intensity) and power efficiency (low heat emission) the light source can be set near the subject to directly irradiate the subject's eye, circumventing the use of optical devices, shutters (and associated light losses) required to direct the light beam to the retina from a remote source.

The invention comprises a variable LED-based light source for visual stimulation constructed with a SLD core device, focusing lens, collimator, and LED controller and driver. When used for retinograms, the controller further controls an electroretinogram device used in retinal examinations and studies (characterizations of light-sensitive cells and devices. The novel LED variable light source may also be utilized to provide light for stimulating a retina during a recording of an eletro-oculogram, a suction electrode ERG, and other like medical and research examinations requiring light to be controlled in frequency, intensity, duration etc.

The benefits of such LED variable light source should be readily recognized by the skilled artisan, and are summarized by category as follows:

1) Cost: LEDs, e.g., SLDs, and respective controllers and driving circuitry are several fold less expensive than incandescent or arc lamps, and their associated power supplies. In particular, the LEDs or SLDs utilized in a preferred embodiment of the invention have a cost of approximately $20, as compared with the cost of a conventional arc lamp as known is approximately $1000. For example, an associated AC/DC power supply for the novel light source, able to supply 1000 mAmp DC has an approximate cost of about $20, where an AC/DC power source for driving a xenon lamp, used in conventional light stimulators typically cost upwards of $5000.
2) Optics: Known light stimulators for use in retinal examinations and research require costly narrow-band chromatic filters (approximately $300 each) to filter portions of the broad frequency range of light sourced by incandescent and arc lamps). Any need for such narrow-band filters are obviated by the novel AED variable light source, and light stimulator including same. And in the inventive AED variable light source, and stimulator including same, a battery of optical density filters, normally costing about $100 each, and required by conventional devices are substituted by a single voltage-controlled liquid crystal attenuation filter, at a cost of about $500, which may drop over time.
3) Durability: A lifetime of an LED or SLD that may be used by the invention remain in spec and operable for well over the 1000 hours average lifetime of incandescent and arc lamps used in conventional devices.
4) Efficiency: As mentioned above, the LED or SLD comprising the AED variable light source of the invention is active only during the flash, and is inactive when the flash is off, which obviates the need for mechanical shutters in the novel constructions. LED power during operation of the novel AED variable light source, and light stimulator including same is approximately 5 Watts, as compared with upwards of 100 W as the standing or continuous power required to drive an incandescent or arc lamp. This is due to the fact that the emission power of the LEDs is concentrated in a narrow bandwidth. For a typical experiment lasting 1 hour a arc lamp would be on for 1 hour expending 100 Watts·hour. For a LED light source assuming a flash every second, the estimated energy expenditure is approximately 0.05 Watts·hour or 2000-fold more efficient. Moreover, the LED-based invention does not require filters in any form.
5) Compact design: The novel AED variable light source and visual stimulator constructed with same does not require mechanical parts such as the shutters and filter wheels required to operate with incandescent and arc lamps of the conventional arts. Electronic control of the light source by way of a controller allows the user to select the characteristics of the flash (color, intensity, timing, multiple flashes), which control may be preset at the controller by way of dials and switches where the controller comprises a mechanical interface, or by a GUI derived from an executable application operating within a computer, e.g., personal computer, for controlling the AED variable light source.
6) Flexibility: The novel controller included with the AED variable light source, and light stimulator constructed with same allows flexibility in the protocol of light stimulation, so important in research and clinical practice. Stimuli consisting of single, paired or trains of pulses of variable color, intensity and duration are readily controlled defined. A trigger pulse input initiates the programmed sequence of flashes.
7) Control: A) Precise control of light intensity by changing the duty cycle of a pulsed signal (frequency >1 MHz) driving the LED. B) Continuous control of the light intensity with a liquid crystal attenuator, as distinguished from available unlike step-wise incremental attenuation control derived from the use of discrete optical filters of prior art devices provides the user with the flexibility required for both clinical retinal examinations and research. Attenuation by the liquid crystal attenuator is controlled by voltage and spans over a 1,000,000-fold range, which may be realized through a cascade construction comprising of 2 liquid crystal attenuators/filters. A similar range of attenuation realized with 'discrete' filters for use with conventional light sources that attenuate at 0.5 log unit increments (3-fold changes) requires 12 filters, and two supporting filter wheels, etc., the cost for which is estimated as amounting to greater than $2000.

BRIEF DESCRIPTION OF THE DRAWING FIGURES

The foregoing and other objects, aspects and advantages will be better understood from the following detailed description of embodiments of the inventions, with reference to the drawings, in which:

FIGS. 2A and 2B are a GUI of a twelve-channel controller for use with the invention;

DETAILED DESCRIPTION OF THE INVENTION

Figure 1:
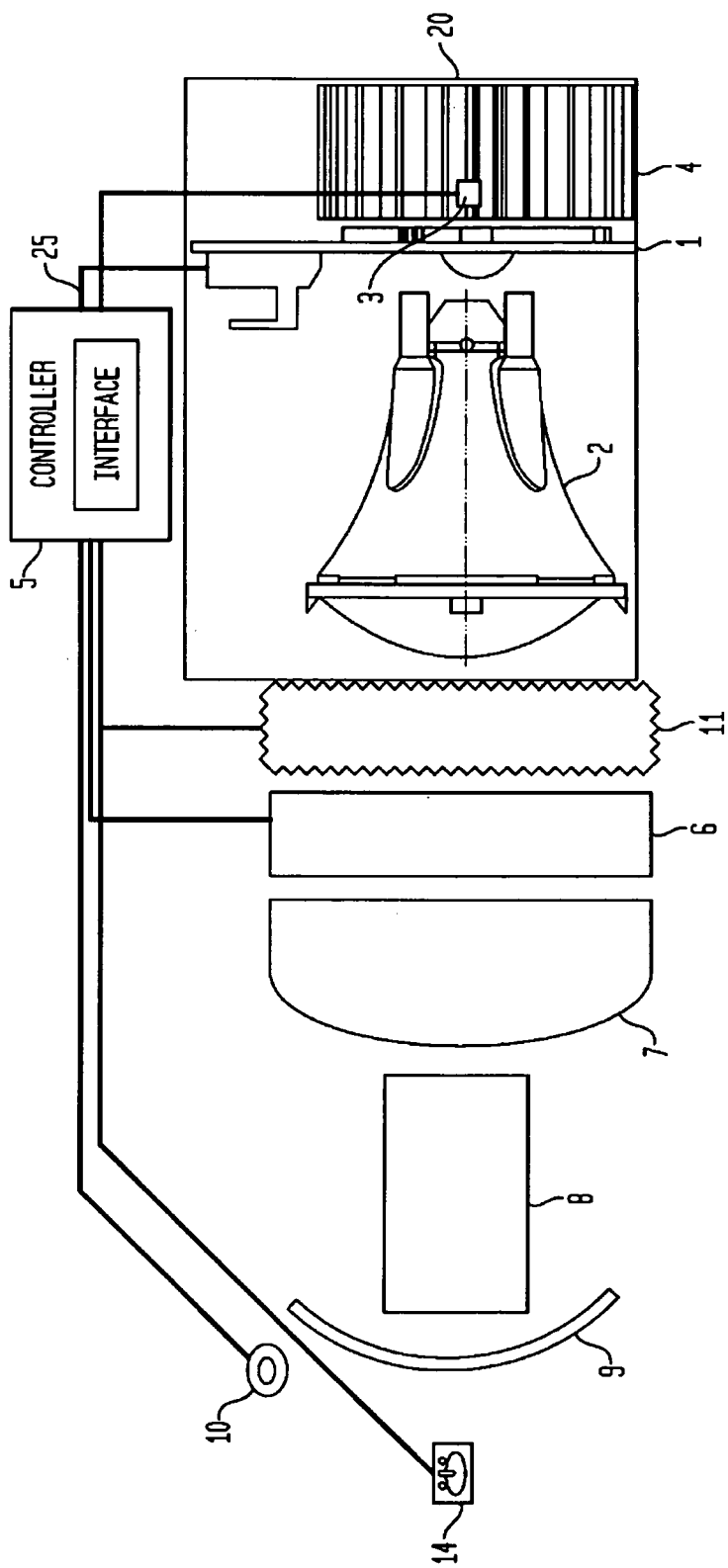
FIG. 1 is a schematic diagram of a first embodiment of an LED-based variable light source of the invention for use in implementing retinograms, including a single channel controller and graphical user interface (GUI) for user access to same.

A LED variable light source, visual stimulator including a novel LED variable light source, and method of conducting a retinal examination by use of the novel LED variable light source are set forth and described herein for the purpose of conveying the broad inventive concepts. The drawings and descriptions provided are not meant to limit the scope and spirit of the invention in any way. To that end, reference will now be made in detail to the present invention, examples of which are illustrated in the accompanying drawings, wherein like reference numerals refer to like elements throughout.

Figure 2B:
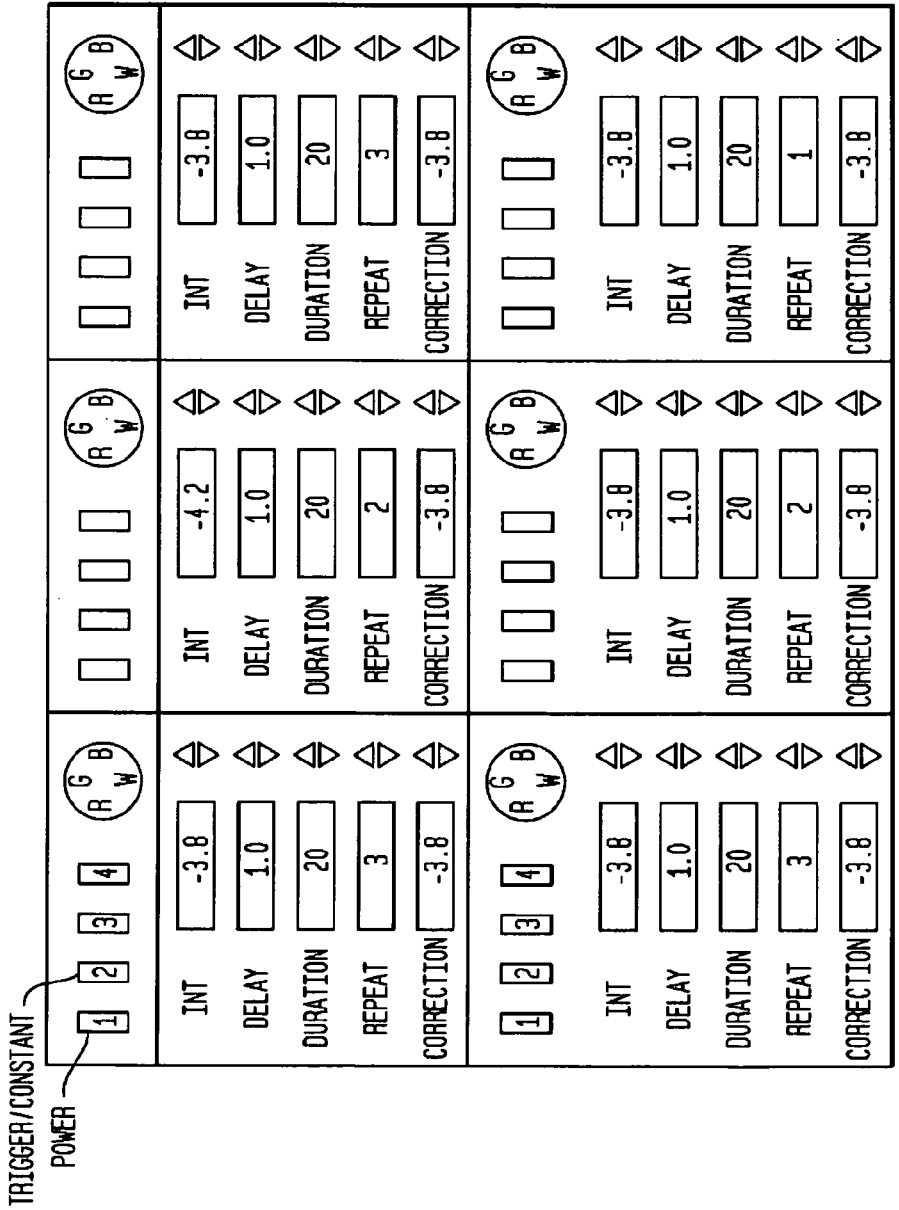
Figure 3:
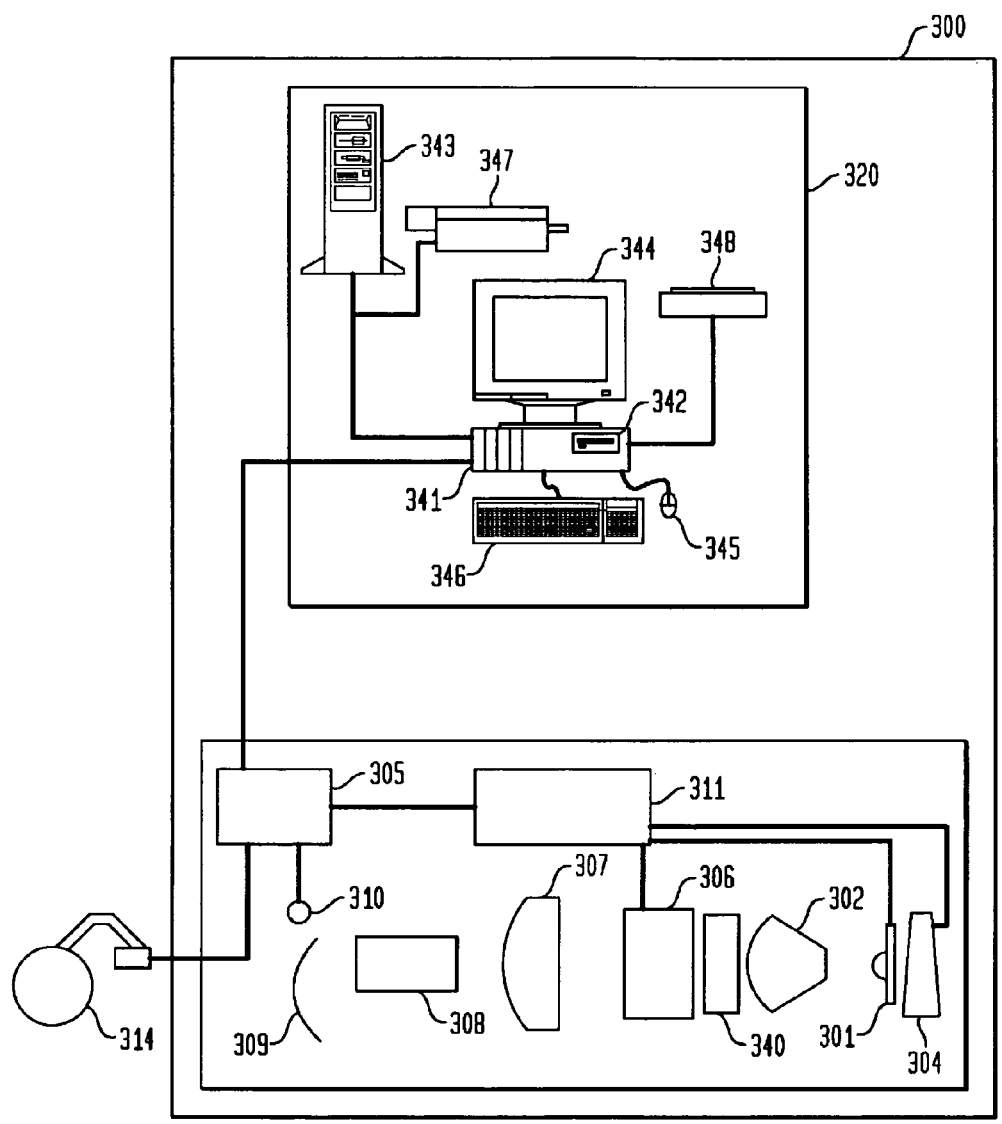
FIG. 3 is a schematic block diagram of a computer system that may be used to control the LED variable light source of the invention.

Via a graphics display on the computer monitor or via settings on a controller (controller box), the user sets the values for the light parameters. The term run as used herein represents a sequence of flashes. Each run is triggered by an input TTL pulse. A plurality of independent flashes can be presented in each run. For example, twelve independent LED units can source twelve different channels of light. A channel as used herein defines the characteristics of every pulse in the run. The user enters the values for the parameters. Options are color (RGBW), delay (DELAY) after the trigger input, duration (DURATION), and intensity (INT). A repeat entry allows presentation of trains of pulses in the same channel. This version of the light source will offer a plurality of channels, for example, twelve. FIGS. 2A and 2B illustrate an example of the graphics/mechanical user interface 25 for control of twelve channels. An extra option is open for future needs.

When a user opts to use the computer, a graphics/mechanical interface (25) communicates (telegraphs) the value of the parameters directly to the controller. In one form, the controller ((5) as depicted in FIG. 1) consists of a power supply, a processing unit and associated A/D and D/A conversion circuitry. The controller (5) also houses the drivers that activate the LEDs. A microprocessor unit, or personal computer (PC) receives the channel information from either the setting on the controller or telegraphed from the computer and formulates a sequence of instructions that will activate the LEDs in accordance to the timing, intensity, and color defined for each channel.

Following the trigger input, the processing unit delivers a series of electrical signals that activate the LEDs and attenuate the light using the voltage-dependent attenuator. A D/A (digital to analog) converter is necessary to convert the digital values generated by the processing unit into analog voltages that control the attenuation of light provided by the liquid crystal attenuator. A feedback system corrects light intensity for losses due to ageing, changes in temperature or slight misalignment. A photodiode (e.g., 10) placed in the light path monitors the intensity of the incident light beam. The feedback signal is digitized by the A/D converter and compared to the instructed value. Any difference prompts the processing unit to introduce corrective action by adjusting the magnitude of the currents delivered to the LEDs.

FIG. 1 represents a first embodiment of a novel, LED variable light source for visual stimulation of the invention.

LEDs are semiconductor devices in which an electrical current is passed through a diode junction to produce light emission in active layers of semiconductor material at the junction. LEDs that operate a relatively high powers and having a relatively broad spectral width are called superluminescent diodes (SLD). While SLDs are known for low modal noise, their spectral width typically decreases with increased coherence as the power driving them increases. By using state-of-the-art ultra bright LEDs (for example, off the shelf LEDs and SLDs manufactured by Lamina Ceramics, Inc., Westhampton, N.J.), the novel LED variable light source of the invention generates "monochromatic" light beams of at least three different colors (red, green, and blue). Alternatively, an LED core provides a range of UV to infra red wave length in the device. In one embodiment, the three different colored light beams may be activated individually, or activated simultaneously in varied intensity to realize a mixed or combined source of mixed wavelength light, essentially allowing the user to create any of a palette of colors from the R, G and B primary colors. Color filters are not required in a light source constructed with such versatile source of raw light.

In the FIG. 1 LED variable light source, LEDs (preferably SLDs) for providing the light to be controlled in the LED variable light source are integrated onto a single LED package or chip (1) for use in one channel. In the embodiment described, the LEDs comprising the chip are disposed on a circular surface of about 3 mm in diameter.

Figure 4:
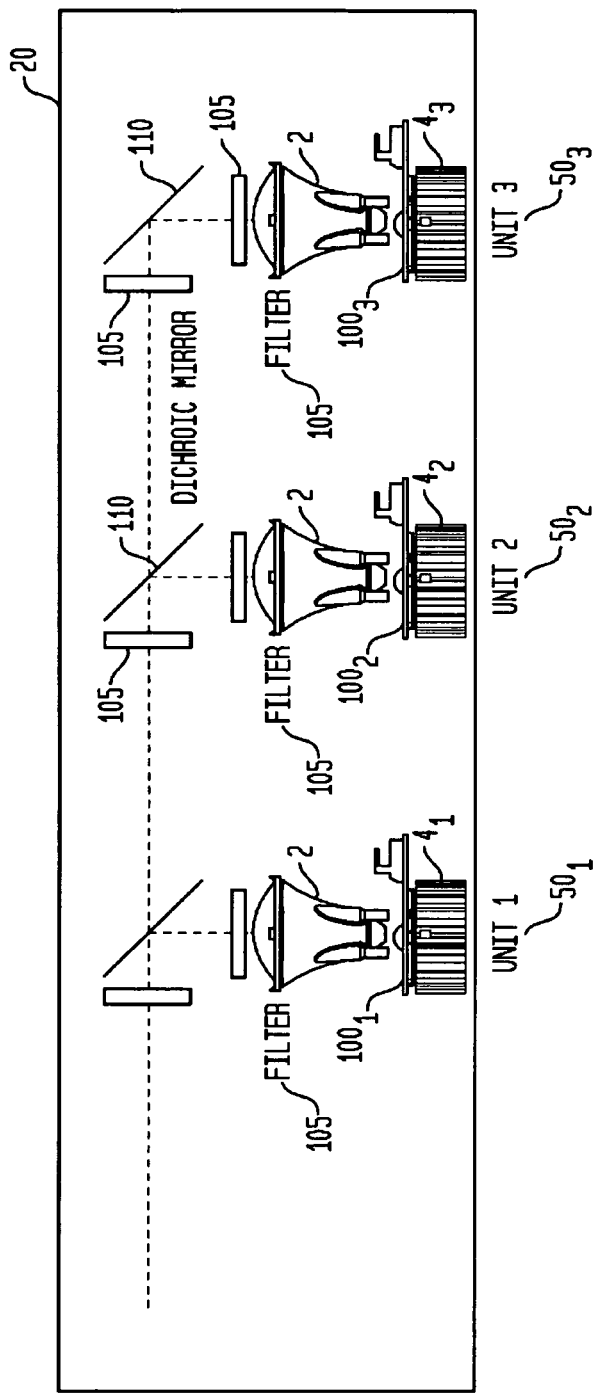
FIG. 4 is a schematic block diagram of the light generating unit according to an embodiment of the invention.

As depicted in FIG. 1, a light generating unit (20) includes a heat sink (4), the LED chip (1) and a narrow lens (2). The LED chip (1) can include a plurality of individual LED units (50). Each unit is separately controlled manually or by a computer. FIG. 4 illustrates a detailed schematic diagram of the light generating unit (20), which will be described in detail later. Light beams radiating from the LED chip are collimated with a narrow lens (2) for controlling and propagating the beams. This results in a compact source of raw light in a very broad spectral range so that a single optical channel can be relied upon to deliver light in any frequency and intensity combination from the three LEDs (comprising the SLD chip or package). FIG. 4 illustrates a light generating unit (20) according to an embodiment of the invention. The light generating unit 20 includes a plurality of individual light source units (50). FIG. 4 illustrates three units; however, any number of units can be used depending on the application. The light source unit 50 comprises a light source (100$_n$), a lens (2$_n$), a heat sink (4$_n$) and a filter (105) (n references the unit number). The filters (105) can be a band pass filter or a neutral density filter. The light source (100) is a LED that is either mono or multi-color. The filters (105) are used for intensity control. The filtered light is reflected by a dichroic mirror (110) to the other components illustrated in FIG. 1. The dichroic mirror (110) reflects concern preset frequencies of light towards the other components. Each dichroic mirror (110) acts as a combining device for combining the individual outputs from each light source unit (50). The output of the dichroic mirror (110) can be filtered by a second filter (referenced as 105). The second filters (105) can also be a band pass filter or a neutral density filter. Each neutral density filter provides more than 3 log units of intensity control. Although, the second filter is references as the same filter, e.g., 105, the filters can be different. For example, one can be a band pass filter while the other can be a neutral density filter.

Light output intensity is on the order of over 100 lumens as driven by up to 5 Watts of DC power. At 5 Watts, the LEDs tend to generate a large amount of heat, particularly at room temperature. Hence an optional heat sink (4) is also shown in the FIG. 1 LED variable light source, which is included to maintain a steady temperature and stable light emission. The temperature of the LED is recorded by a controller (5), preferably continuously using a heat sensor (3). The lifetime of such LEDs is rated at 20K (20,000) hours.

In an embodiment of the invention, a separate tunable filter (11) is positioned between the light generating unit (20) and attenuators (6). By including the tunable filter, the chromatic resolution is improved. For example, a tunable filter (11) is used where a narrow-band of color light is needed in the application. In an embodiment, the tunable filter, or tunable optical filter operates in a wavelength range of 350-2500 nm. The bandwidth of the light, measured as full width at half max is 5 nm for wavelengths between 420-1000 nm. In an embodiment, the tunable filter (11) can be set to have a tuning resoluation of 0.1 nm and a 7° field of view, where the switching speed is less than 100 msecs and operated in a 10-35° C. temperature range. The tunable filer, for example, can be manufactured by Meadowlark Optics, Inc.

Onset and offset of the light beams, as well as an intensity of the light beams is controlled electronically by controller (5), electrically connected to the LED (1) and the attenuators (6) by activating or inactivating the respective LEDs, and adjusting attenuation using a graphics/mechanical user interface (25). The controller (5) includes a graphic/mechanical user interface (25), an example of which is depicted in FIGS. 2A and 2B. Light intensity is controlled with liquid crystal attenuators (6) positioned in the path of the collimated light beam after being collimated in lens (2). When the electronics control of the LED intensity is added to the filters (105), intensity control, the outgoing light can be controlled using a 7 log intensity control. The outgoing light is detected by a photodiode (10) and reported to the controller (5) for feedback control of the each individual light source unit (50).

Each liquid crystal attenuator (6), for example, as manufactured by Meadowlark Optics, Inc., provides up to 1000-fold (3 log) variable attenuation on a continuous light beam. The degree of attenuation is controlled electronically by controller (5). Arranging two attenuators, e.g., (6) in series (cascade), therefore, results in an up to 1,000,000-fold attenuation. The small size of the attenuator housing lends to the overall compact design of the LED variable light source of the invention. The light intensity is also controlled electronically via a controller (5) by varying a duty cycle of a pulsed electrical signal. The attenuation range is 1000-fold for each unit.

The controller 5 can include a separate driver, such as the GUI (25), an example is illustrated in FIGS. 2A and 2B. The GUI (25) is coupled to a control box. The GUI is in electrical communication with the control box.

Alternatively, the control may also take the form of a GUI generated and displayed by a PC. The PC may be controlled to implement the GUI, and the signals required to control the controller (5) by use of a set of executable instructions for carrying out the driver functions required. Onset and offset times are in the order of 100 nanoseconds (100×10-9 seconds). Mechanical shutters (diaphragms) are not required. Controller (5), is connected to a PC ((not shown), the heat sink (4), a graphics/mechanical user interface (25), photodiode (10) and subject, such as electroretinogram recording device (14)).

The LED variable light source construction with heat sink in its optimal packaging is designed to be less than 27 cubic inches (3 in.×3 in.×3 in.), which can be placed near the subject (eye, or other light sensitive cells and devices) for direct light stimulation. Alternatively, the LED variable light source construction includes a collimator (7) by which the attenuated beam emanating from attenuator(s) (6) can be better focused. The focused output from collimator (7) is provided to and carried by a fiber optic (8) or light pipe, for delivery to a subject at the other or far end of the fiber optic (8).

A secondary lens (9), or diffuser may be included in the LED variable light source to further alter outgoing light for fiber optic (8). A photodiode (10) is also preferably included in the LED variable light source to monitor intensity and frequency of the light output, which as mentioned above is connected to and controlled by controller (5). The photodiode (10) monitors the light beam by sampling the beam and generating a correcting feedback signal that is used by the controller, and or the executable program operational within PC to control the power delivered to the LEDs. The light beam color, light beam intensity, and light beam output timing (onset and offset times) is controlled electronically by way of controller (5).

Two or more of these LED variable light sources may be arranged to operate together as a light module by which combinations of light pulses and background stimulus may be readily generated to facilitate many variations of retinal stimulation. FIGS. 2A and 2B herein shows a graphics/mechanical userinterface (25) arranged for controlling twelve (12) LEDS or SLDs operating in twelve (12) channels. And as mentioned above with respect to the FIG. 1 embodiment, while shown as a graphics/mechanical user interface (25), with corresponding controls for each individual channel, the interface is readily implemented by a computer driven GUI, that may provide the control for the controller, to control the various above described components of the LED variable light source, and its variations.

That is, the GUI control for the controller (5) will generally be implemented by a computer executing a sequence of program instructions for carrying out the steps of the method, assuming all required data for processing is accessible to the computer. The sequence of program instructions may be embodied in a computer program product comprising media storing the program instructions. As will be readily apparent to those skilled in the art, the present invention can be realized in hardware, software, or a combination of hardware and software. Any kind of computer/server system(s)—or other apparatus adapted for carrying out the methods described herein—is suited. A typical combination of hardware and software could be a general-purpose computer system with a computer program that, when loaded and executed, carries out the method, and variations on the method as described herein. Alternatively, a specific use computer, containing specialized hardware for carrying out one or more of the functional tasks of the invention, could be utilized.

Another embodiment of an AED variable light source 300 of the invention comprises a personal computer (PC) system (320) for controlling a controller (305), comprising the novel light source. The PC system or PC (320) is arranged to control the controller (305), which controls the user interface (311), the photodiode (310), and the electroretinogram device (314), shown in the figure but not part of the novel AED variable light source (300). The user interface controls LED (301), heat sink (304), and attenuators (306). A lens (302), a collimator (307), fiber optic (308) and diffuser (309) are also included in the LED variable light source. Optionally, a tunable filter (340) is used to improve the chromatic resolution, in the same manner as described above.

PC (320) provides an executable method for implementing the controls for controlling the LED variable light source to carry out retinal stimulation for examinations and research. Controller (305) is essentially controlled by the PC system (320) including a processing unit (341), which houses a processor, memory and other systems components that implement a general purpose processing system or computer that may execute a computer program product. The computer program product may comprise media, for example a compact storage medium such as a compact disc, which may be read by the processing unit (341) through a disc drive (342), or by any means known to the skilled artisan for providing the computer program product to the general purpose processing system for execution thereby.

The computer program product comprises all the respective features enabling the implementation of the LED variable light source and methods of operating same as described herein, and which method of computer instructions, or executable application embodying a computer program product—when loaded in a computer system—is able to carry out these methods. Computer program, software program, executable program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The computer program product may be stored on hard disk drives within processing unit (341, as mentioned) or may be located on a remote system such as a server (343), coupled to processing unit (341), via a network interface such as an Ethernet interface. Monitor (344), mouse (345) and keyboard (346) are coupled to the processing unit (341), to provide user interaction. Scanner (347) and printer (348) are provided for document input and output. Printer (348) is shown coupled to the processing unit (341) via a network connection, but may be coupled directly to the processing unit. Scanner (347) is shown coupled to the processing unit (341) directly, but it should be understood that peripherals may be network coupled, or direct coupled without affecting the ability of the processing unit (341) to perform the method of the invention.

Although examples of the present invention have been shown and described, it would be appreciated by those skilled in the art that changes may be made in these embodiments without departing from the principles and spirit of the invention, the scope of which is defined in the claims and their equivalents.

What is claimed is:

1. A LED variable light source, comprising: a super luminescent LED for generating a light signal; a light lens for receiving and focusing the generated light signal; and a controller for controlling the light signal's intensity via a driver interface, constructed and arranged to allow a user to input LED variable light source control inputs; wherein the LED is driven by a pulsed signal, and the controller controls the intensity of the light signal generated by the LED by changing the duty cycle of the pulsed signal.

2. The LED variable light source as set forth in claim 1, further comprising a light attenuator, controlled by the controller, for attenuating of the focused light signal.

3. The LED variable light source as set forth in claim 1, further comprising a collimator for collimating the light signal.

4. The LED variable light source as set forth in claim 1, further comprising a light guide for carrying the collimated, focused, attenuated light signal.

5. The LED variable light source as set forth in claim 1, further comprising a diffuser for maintaining the coherence of the light signal.

6. The LED variable light source as set forth in claim 1, further comprising a heat sink and heat sensor, controlled by the controller, which together support maintaining the super-luminescent LED in a fixed temperature range.

7. The LED variable light source as set forth in claim 6, further comprising a photodiode, in communication with the controller, for receiving some portion of the light signal and generating a feedback signal to be used by the controller to moderate both a frequency and intensity of the light signal.

8. The LED variable light source as set forth in claim 1, further comprising a computer processor, in communication with and for controlling the controller, and providing a driver interface in a form of a graphical user interface (GUI) in a display associated with the computer processor, constructed and arranged to allow a user to input LED variable light source control inputs.

9. The LED variable light source as set forth in claim 1, further comprising: a collimator for collimating the focused, attenuated light signal; a light guide for carrying the collimated, focused, attenuated light signal; and a diffuser for maintaining the coherence of the collimated, focused, attenuated light signal.

10. The LED variable light source as set forth in claim 1, further comprising a tunable filter for reducing a bandwidth of the generated continuous light signal output from the lens.

11. The LED variable light source as set forth in claim 1, further comprising a plurality of super luminescent LEDs for generating a multiple continuous light signals, each LED driven by a pulsed signal, and the intensity of the light signal generated by each LED controlled by changing the duty cycle of the pulsed signal.

12. The LED variable light source as set forth in claim 1, wherein each of the continuous light signals are separately controllable.

13. The LED variable light source as set forth in claim 1, further comprising a plurality of a dichroic mirrors, each dichroic mirror reflects a specific continuous light signal towards at least one attenuator.

14. The LED variable light source as set forth in claim 1, further comprising a plurality of filters positioned between each super luminescent LED and a dichroic mirror for adjusting the intensity of a specific continuous light signal.

15. The LED variable light source as set forth in claim 14, wherein the filters are a neutral density filter.

16. The LED variable light source as set forth in claim 1, wherein said light source generates light in a wave length from UV to infra-red.

17. The LED variable light source as set forth in claim 16, wherein said light is deliverable in a 5 nm bandwidth.

18. The LED variable light source as set forth in claim 1, wherein the frequency of the pulsed signal is greater than about 1 MHz.

19. A visual stimulator for stimulating retinal responses, comprising: a LED variable light source for providing and moderating a continuous light signal to best suit an intended retinal examination; a controller for controlling the LED variable light source to moderate and direct the light signal into the retina; and a retinal response recorder for recording retinal responses to said moderated light signal; wherein the LED variable light source comprises: a light lens for focusing the generated light signal; a collimator for collimating the focused, attenuated light signal; a light guide for carrying the collimated, focused, attenuated light signal; and a diffuser for maintaining the coherence of the collimated, focused, attenuated light signal, wherein the controller controls the intensity of the light signal provided by the LED by changing the duty cycle of a pulsed signal driving the LED.

20. The visual stimulator as set forth in claim 19, further including a processor for receiving and processing the signal response.

21. The visual stimulator as set forth in claim 20, further comprising a photodiode for receiving some portion of the light signal and generating a feedback signal therefrom for use by the controller in moderating both a frequency and an intensity of the light signal.

22. The visual stimulator as set forth in claim 20, wherein the frequency of the pulsed signal is greater than about 1 MHz.

23. The visual stimulator as set forth in claim 20, further comprising a light attenuator for attenuating of the focused light signal.

* * * * *